United States Patent [19]
Curry et al.

[11] Patent Number: 5,855,138
[45] Date of Patent: Jan. 5, 1999

[54] TORSION SPRING GRADING BY HYSTERSIS AVERAGING

[75] Inventors: Steven Alan Curry, Nicholasville; Benjamin Keith Newman, Lexington, both of Ky.

[73] Assignee: Lexmark International, Inc., Lexington, Ky.

[21] Appl. No.: 977,532

[22] Filed: Nov. 25, 1997

[51] Int. Cl.$^6$ .................................................. G01L 3/00
[52] U.S. Cl. ............................................................ 73/161
[58] Field of Search ...................... 73/161, 1.09, 1.54, 73/1.55, 847, 836, 789; 338/5

[56] References Cited

U.S. PATENT DOCUMENTS

| | | | |
|---|---|---|---|
| 964,743 | 7/1910 | Bindschedler | 73/161 |
| 1,120,838 | 12/1914 | Miller | 73/161 |
| 1,624,303 | 4/1927 | Zesinger | 73/161 |
| 2,182,519 | 12/1939 | Handy et al. | 73/161 |
| 2,765,655 | 10/1956 | Scott | 73/161 |
| 3,479,858 | 11/1969 | Umeno et al. | 73/15.6 |
| 3,638,230 | 1/1972 | Umeno et al. | 346/33 R |
| 3,939,920 | 2/1976 | Hardiman et al. | 173/1 |
| 3,982,419 | 9/1976 | Boys | 73/139 |
| 5,324,011 | 6/1994 | Vilches et al. | 73/161 |
| 5,460,052 | 10/1995 | Ertürk et al. | 73/847 |
| 5,634,169 | 5/1997 | Barry et al. | 399/12 |

*Primary Examiner*—Ronald Biegel
*Attorney, Agent, or Firm*—John A. Brady

[57] ABSTRACT

Torsion springs (1) are graded by both winding and unwinding them in a test fixture (20) having a central arbor (52a) and ledges (54,58) functionally corresponding to the use of the springs. This takes hysteresis into account. Data obtained at a known location is approximated as separate straight lines for winding and unwinding. The rotation at the predetermined base or preload torque is determined from the straight lines, and the two values are averaged. To this average value a large predetermined amount (70 degrees) of rotation is added, the torque at that value of rotation is determined from the straight lines, and the two values are averaged. The spring is graded as acceptable when that average torque is within a predetermined range.

4 Claims, 6 Drawing Sheets

TORSION SPRING GRADING BY HYSTERSIS AVERAGING

TECHNICAL FIELD

This invention relates to the measuring of the characteristics of torsion springs so that they can be graded as either satisfactory or unsatisfactory for particular requirements.

BACKGROUND OF THE INVENTION

U.S. Pat. No. 5,634,169 to Barry et al. discloses a coupling of two rotatable members through a torsion spring. The first rotatable member is drive member of predetermined torque and the second, driven member drives a paddle in a toner hopper. The amount of deflection of the torsion spring is employed to sense the amount of toner in a hopper. In such an application, the torque characteristics of the spring must be within predetermined limits or the measurement of toner will not be sufficiently accurate.

Accordingly, characteristics of springs for such a use are measured so as to grade the spring as within acceptable range of characteristics or not. The previous known methods of grading torsion springs measures spring characteristics at particular amounts of deflection. However, this has proved not to be an accurate method of measurement.

DISCLOSURE OF THE INVENTION

This invention includes a recognition that torsion springs have different characteristics of response during winding and unwinding. Springs under measurement are wound and their reaction torque is measured at a series of known wound positions. This data is subsequently described as its linear approximation from relaxed to a predetermined "pre-load" or "base" torque. The data from torque higher than the base torque is subsequently described as its linear approximation from a rotation point past the base torque to the highest torque of possible interest. The wound springs are unwound and their reaction torque is measured at a series of known positions during unwinding. That data is subsequently described as its linear approximation from relaxed to the base torque. That data is also subsequently described as its linear approximation from a rotation point past the base torque to the highest torque of possible interest. Because of hysteresis, the base torque occurs at two different rotations, one during winding and one during unwinding. The average rotations of those different base torques taken, and the data for greater rotations is examined to determine the average torque at a predetermined rotation greater than that average rotation at base torque. Because of hysteresis, the torque found at that rotation will have two values. Those two values are averaged, and the spring from which the data was obtained is graded on the basis of that average torque.

BRIEF DESCRIPTION OF THE DRAWINGS

The details of this invention will be described in connection with the accompanying drawings, in which.

DESCRIPTION OF THE PREFERRED EMBODIMENT

Figure 1:
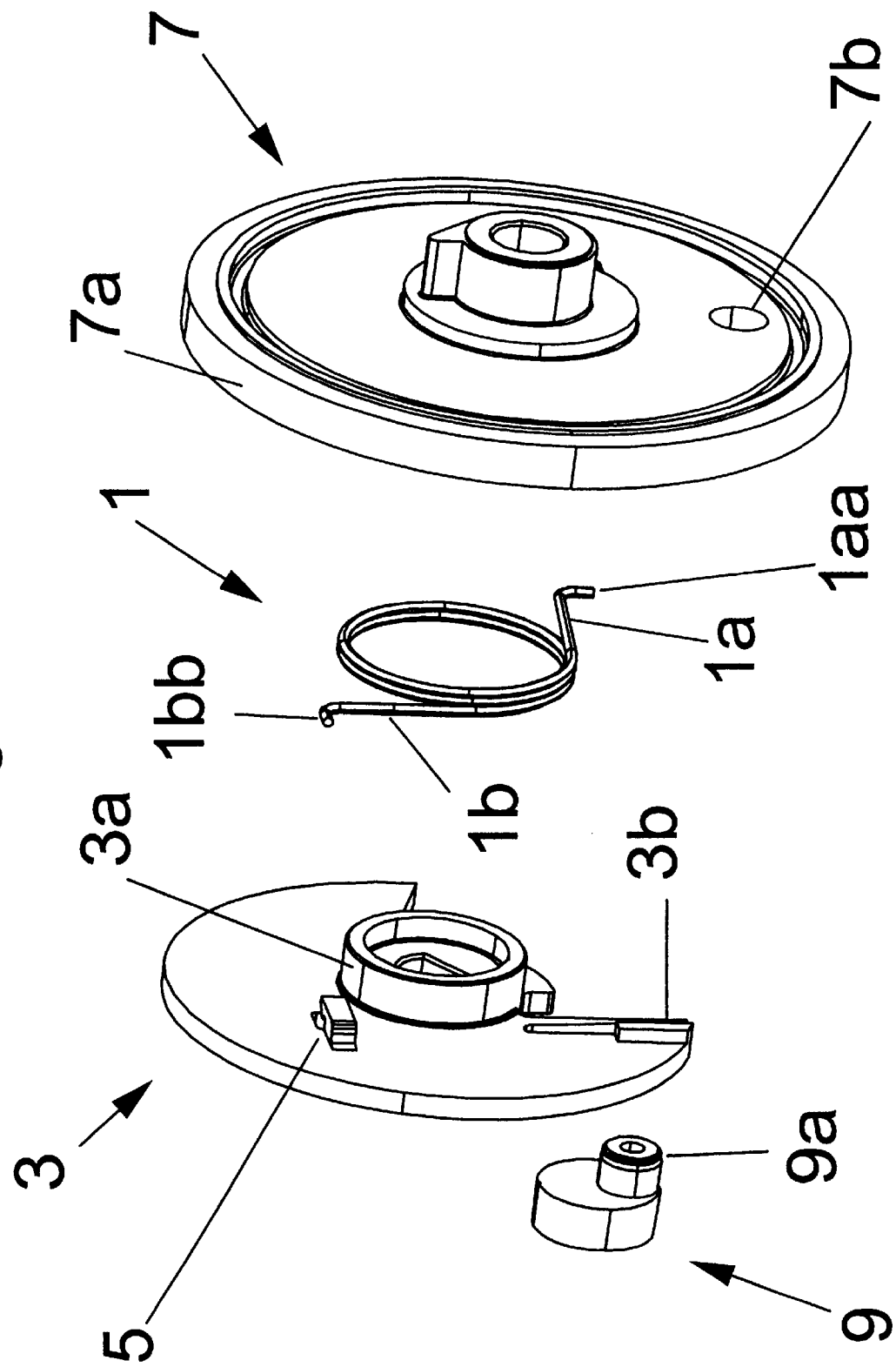
FIG. 1 is a exploded view of a torsion spring of interest in its application setting.

As shown in FIG. 1, the torsion spring 1 of interest is a single, steel wire (high carbon, hard drawn music wire) formed into two loops and a partial third loop (specifically 2.24 coils) with a straight end section 1a on one end of spring 1 having a perpendicular end tab 1aa, and a straight end section 1b on the other end of spring 1 having a perpendicular end tab 1bb. The spring as just described and as shown in FIG. 1 is in its relaxed condition.

A driven member 3 of hard plastic has a cylindrical arbor 3a on which spring 1 loosely fits around (relaxed inside diameter of spring 1 is 18 mm; outside diameter of spindle 3a is 15 mm). Straight end 1b of spring 1 is held in ledge member 5, which is integral with member 3. Arm 3b, which is integral with member 3 for tension adjustment and is not significant with respect to the instant invention. All of the members 3, spindle 3a, ledge member 5, and arm 3b are a single part of continuous, hard plastic formed by conventional molding.

Driving member 7 is also a single part of continuous, hard plastic formed by conventional molding. Member 7 is a circular gear having teeth on its outer periphery 7a (teeth not shown) and a hole 7b which receives stud 9a of eccentric member 9.

Figure 2:
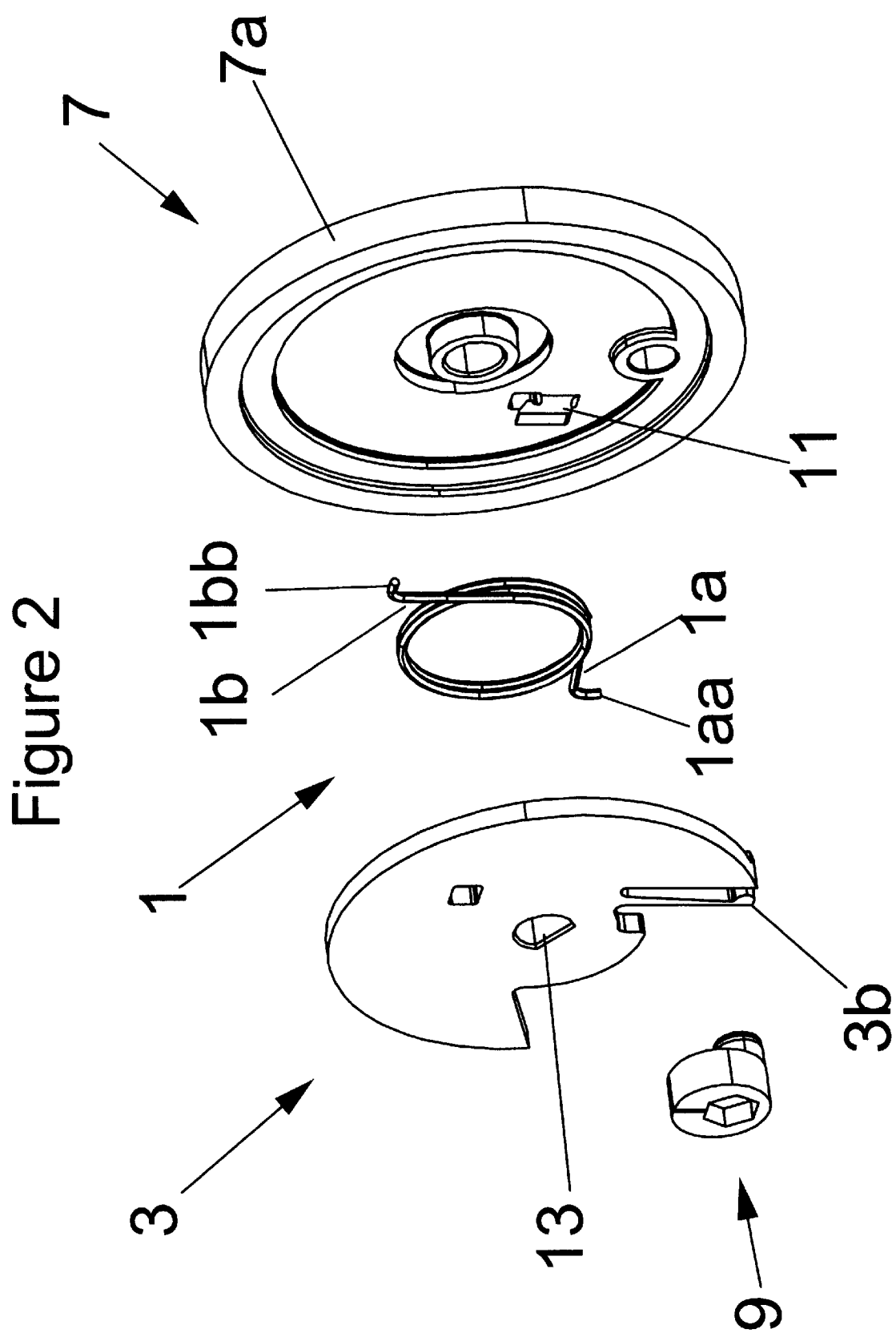
FIG. 2 is a view similar to FIG. 1 from a direction opposite to the direction of view of FIG. 1.

Referring to FIG. 2, driving member 7 has on its inner face a ledge member 11 integral with member 7 which receives straight end 1a of spring 1. In use spring 1 is supported on spindle 3a and held against relaxed rotation by ledges 5 and 11. Tab ends 1aa and 1bb encounter ledges 5 and 11 respectively to prevent spring 1 from moving out of contact with ledges 5 and 11 respectively. During initial assembly, eccentric 9 is rotated against arm 3b to achieve a predetermined base torque on spring 1.

In operation driving member 7 receives torque at periphery 7a from a motor in a printer. This moves driving member 7 in a direction for ledge 11 to push end section 1a to wind spring 1. This winding of spring 1 applies a rotating force on driven member 3 through end section 1b pushing on ledge 5. The amount of winding of spring 1 to achieve movement of member 3 is dependent on the resistance of a shaft (not shown) attached to member 3 by being physically keyed to central hole 13.

The purpose of this invention is to measure the characteristics of springs intended for use as a spring 1 to assure that it is within the range of characteristics for which the assembly of FIGS. 1 and 2 are designed.

Figure 3:
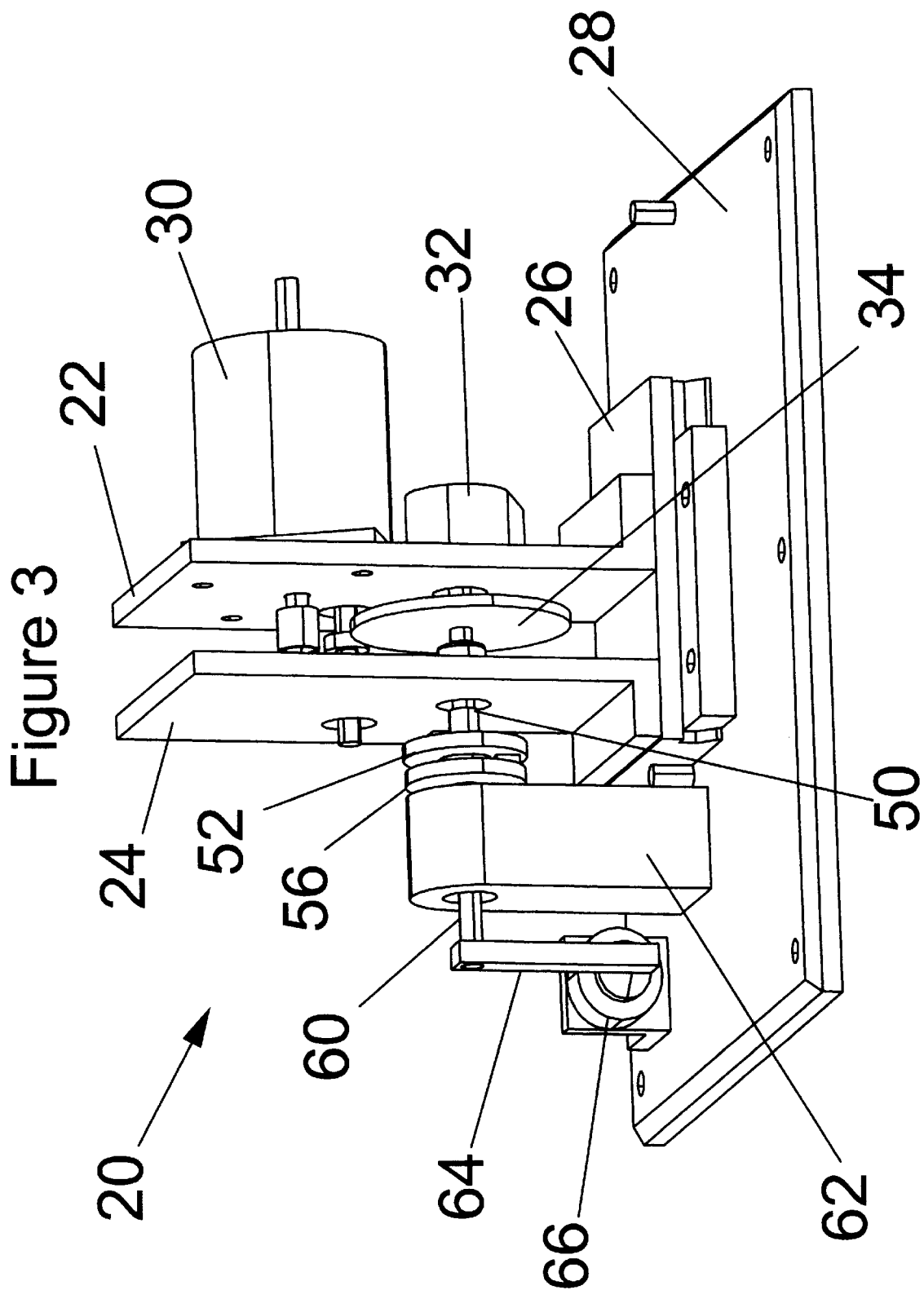
FIG. 3 is a perspective view of a preferred test fixture.
Figure 4:
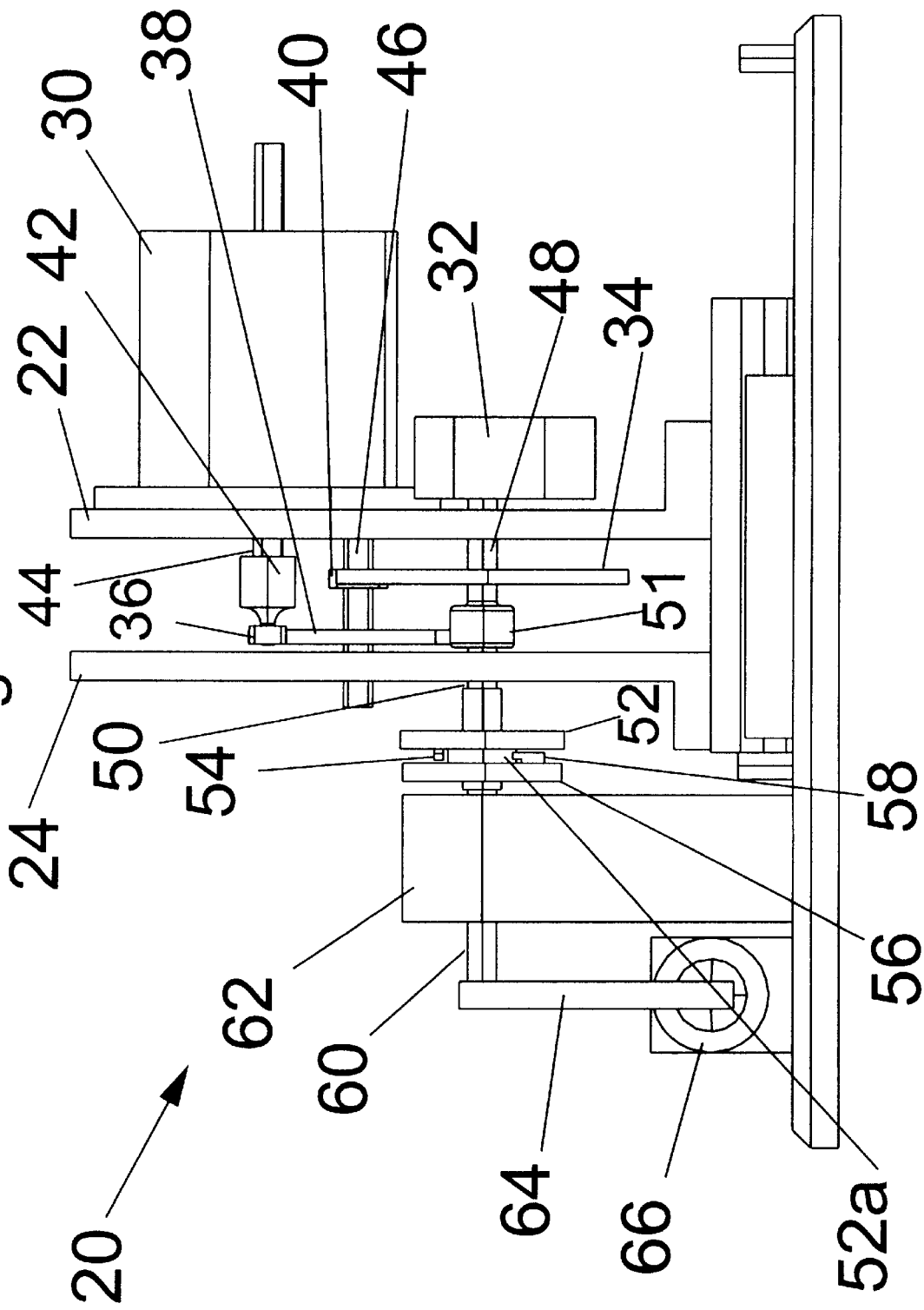
FIG. 4 is a side view of the test fixture of FIG. 3.

FIG. 3 is a test fixture 20 which implements the data gathering of this invention. Fixture 20 has upright support plates 22 and 24 spaced from each other in parallel posture, both supported on a base 26, which is supported on a larger base 28. Plate 22 supports motor 30, which extends outward from plate 22. Plate 22 similarly supports optical encoder 32 which senses holes in an internal disk which rotates with gear 34. As best shown in FIG. 4, plates 22 and 24 support a reduction gear train of small gear 36, large gear 38 which is driven by gear 36, small gear 40 which turns with large gear 38, and large gear 34, which is driven by gear 40. Gear 36 is driven through coupler 44 of motor 30. Shaft 46 is supported by plates 22 and 24 and is keyed to gears 38 and 40. Shaft 48 is supported by plate 22 and is keyed to gear 34. Shaft 48 drives output shaft 50 through coupler 51. Base 26 slides on base 28 to facilitate installation and removal spring 1 with respect to the test fixture 20.

Shaft 50 is integral with drive plate 52, which faces plate 56. Plate 56 has a ledge 58 which is substantially identical in form to ledge 11. Plate 52, is a circular disk, not a partial disk as is member 3, but is substantially identical to member 3 in having a ledge 54 which is substantially identical in form to ledge 5 and which is located at the same orientation to ledge 58 on plate 56 as ledge 5 is located to ledge 11. Drive plate 52 has a central arbor 52a which is substantially identical in form to arbor 3a. However, the materials of the test fixture differ from that of members 3 and 7 for durability. In particular the material of spindle 52a is metal, while that of spindle 3a is of the same hard plastic as that of member 3. Also arbor 52a is integral with the drive plate 52, while arbor 3a is integral with driven member 3. These two difference do not result in a significant alternation the winding and unwinding characteristics of spring 1 as measured by test fixture 20 as here described.

Shaft 60 extends from and is integral with member 56. Shaft 60 is rotatably supported in tower 62, which is mounted on base 28. Shaft 60 is keyed to arm 64, which contacts load cell 66(an electronic strain gage), which is mounted on base 28.

Figure 5:
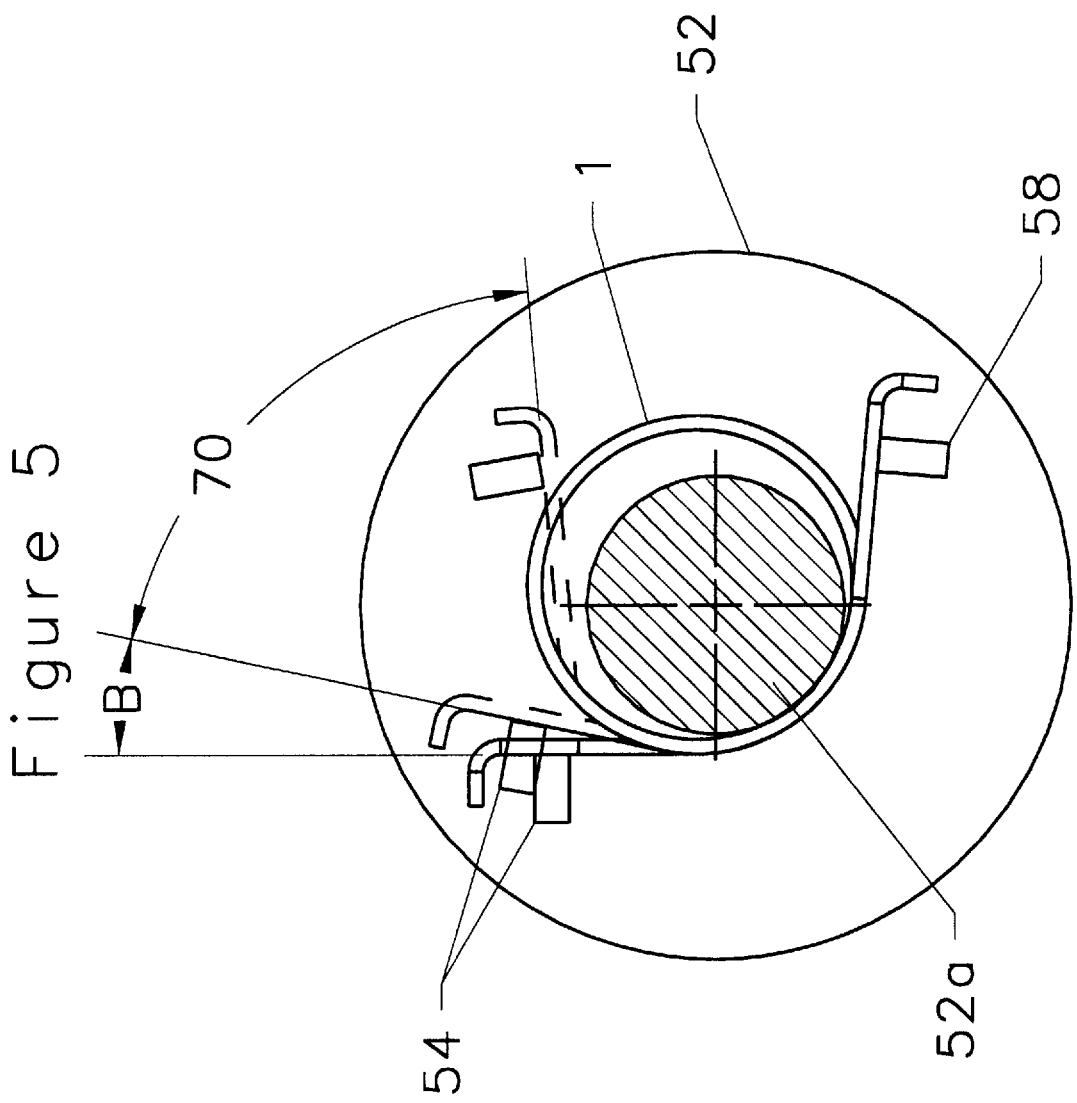
FIG. 5 is a front view of the driving member of the test fixture with the spring and in two positions of rotation.

FIG. 5 is a front view of the driving member 52 with a spring 1 illustrating the ledges 54 and 58 with spring 1 in the relaxed position and the ledges 54 and 58 with spring 1 in an ideal position of 70 degrees rotation past the base position (the base rotation is shown as B in FIG. 5). This also illustrates the loose fit between the spring 1 and arbor 52a.

Encoder 32 is a commercially available device understood to be of essentially standard design in which a disk in the device turns with the input shaft and a series of equally spaced holes (or spots in the case of reflective sensing) are sensed using light. In test fixture 20 shaft 48 drives such a disk and encoder 32 produces an electrical pulse for every 7/20th of a degree (200 pulses equal 70 degrees). Also not shown is computer controlled electrical connections as that may be entirely straightforward and conventional.

Operation of fixture 20 is by driving the encoder first for 280 pulses in the direction of winding spring 1 and then in the reverse 280 pulses which unwinds spring 1. A spring 1 to be graded is first inserted between members 52 and 56 by sliding member 52 away from member 56. The spring 1 is located on arbor 52a and held on ledges 58 and 54 in a manner substantially identical in position as the mounting of spring 1 on ledge 5 and ledge 11 respectively. Member 52 is then slid toward member 56 until base 26 encounters a stationary blocking member (not show). Under computer control motor 30 then is started and stopped, each signal from encoder 32 is interpreted a 7/20 degree rotation of drive member 52, and the torque sensed at load cell 66 is recorded for each signal from encoder 32.

Figure 6:
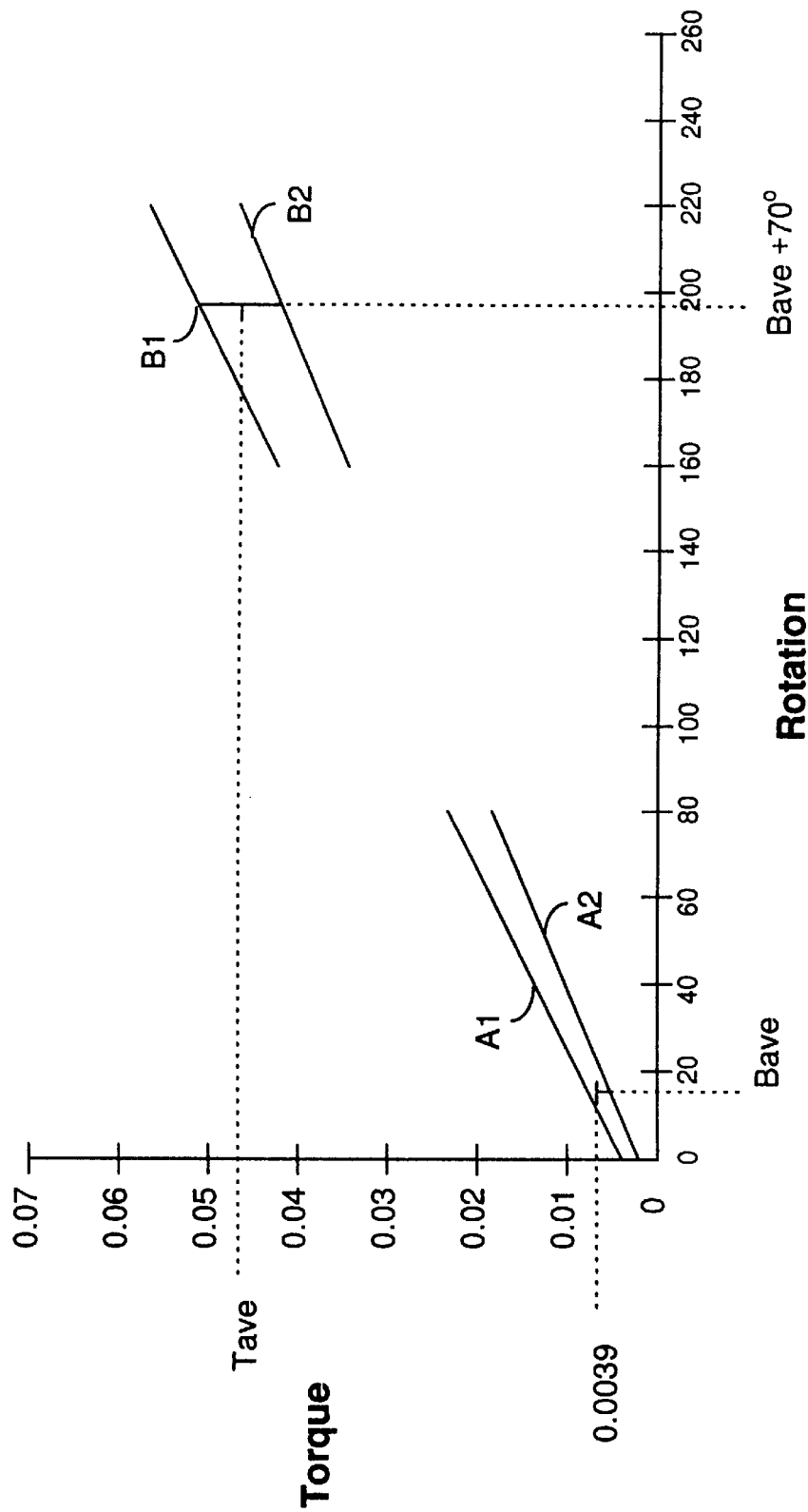
FIG. 6 illustrates the relationships determined from test data.

This data is then interpreted as follows: The data of the first 80 pulses during winding is employed to compute a straight line approximation of that data. The data of pulses 160 to 240 during winding is employed to compute a straight line approximation of that data. The data of the first pulses 41 to 161 (absolute position 240 to 160 from the relaxed origin) of the unwinding operation is employed to compute a straight line approximation of that data. The data of pulses 200 to 279 (absolute position 80 to 1 from the relaxed origin) unwinding operating is employed to compute a straight line approximation of that data. The two lines from between relaxed and 80 pulses are examined to determine the rotation at 0.0039 inch ounces of torque, which is the base or preload torque for the preferred spring 1. The average of the two rotations is determined (as by adding them and dividing by 2). This produces a single, computed base rotation, termed Bave in FIG. 6. The two lines from between 160 and 240 pulses are examined for the torque observed at 70 degrees rotation plus Bave the single, computed based rotation. The average of the two torques is determined (as by adding them and dividing by 2). This single, computed torque, termed Tave in FIG. 6, is the value by which the spring 1 under test is graded. The preferred spring must be within plus or minus 0.003 ounce inches of 0.048 ounce inches to be acceptable for the intended use.

FIG. 6 illustrates the relationships determined. The horizontal axis is degrees of rotation of spring 1 and the vertical axis is torque as sensed by load cell 66 in ounce inches. The winding of spring I invariable produces higher torques for a given degree of rotation and then the unwinding of spring 1. This is believed to be because of interaction with the center arbor 3a, 56a. This invention takes that into account. In the straight lines A1, A2 from the origin to 8 degrees (80 pulses from encoder 32), the top line A1 is the linear approximation of data while winding, and the bottom line A2 is the linear approximation of data while unwinding. The base torque of 0.0039 ounce inches is seen to be at less than 8 degrees, and the average rotational position of spring 1 at the base torque falls between the two lines A1 and A2 and occurs at a location representing a rotation Bave. With the rotation amount Bave known, 70 degrees is added to that rotation.

Top straight line B1 is the linear approximation of the data from winding from 56 degrees (160 pulses from encoder 32) to 84 degrees (240 pulses from encoder 32). Bottom straight line B2 is the linear approximation of the data from unwinding from 84 degrees to 56 degrees. The torque represented in straight lines B1, B2 from rotation of Bave plus 70 degrees is seen to be two torques and the average of those torques Tave, of course, falls between the two lines. Tave is the ultimate value sought for grading spring 1.

Although not conceptually necessary, the computations are done by computer, using standard routines. It is assumed that the computation of straight line information is by the standard, least squares formula, although any reasonably accurate computation would suffice.

None of the foregoing computation are highly critical and so they may be made by reasonable approximation rather than exactly. Although approximating the low torque data as a line separately from the high torque data is more accurate, approximating of all the tightening data as a single straight line and approximating all of the loosening data as a second single straight line is believed to be sufficiently accurate for some purposes. Other variations employing this invention will be apparent and can be anticipated.

What is claimed is:

1. The method of grading a torsion spring comprising the steps of:

winding said torsion spring while measuring the torque of said spring at known locations of rotation, unwinding said torsion spring while measuring the torque of said spring at known locations of rotation, approximating said measurements from winding as a first straight line, approximating said measurements from unwinding as a second straight line, determining a first rotation represented by said first straight line at a predetermined base torque, determining a second rotation represented by said second straight line at said predetermined base torque, determining approximate average rotation of said first rotation and said second rotation, determining a first torque represented by said first straight line at a rotation of said approximate average rotation plus a predetermined rotation, determining a second torque represented by said second straight line at a rotation of said approximate average rotation plus a predetermined rotation, determining approximate average torque of said first rotation and said second rotation, and grading said spring with respect to operation in which said spring is wound and unwound while loosely supported on an arbor on the basis of said approximate average torque.

2. The method of claim 1 in which said predetermined rotation is about 70 degrees.

3. The method of grading a torsion spring comprising the steps of:

winding said torsion spring while measuring the torque of said spring at known locations of rotation, unwinding said torsion spring while measuring the torque of said spring at known locations of rotation, approximating low torque measurements of said winding as a first straight line, approximating high torque measurements of said winding as a second straight line, approximating low torque measurement of said unwinding as a third straight line, approximating high torque measurements of said unwinding as a fourth straight line, determining a first rotation represented by said first straight line at a predetermined base torque, determining a second rotation represented by said third straight line at a predetermined base torque, determining approximate average rotation of said first rotation and second rotation, determining a first torque represented by said second straight line at a rotation of said approximate average rotation plus a predetermined rotation, determining a second torque represented by said fourth straight line at a rotation of said approximate average rotation plus a predetermined rotation, determining approximate average torque of said first torque and said second torque, and grading said spring with respect to operation is which said spring is tightened and loosened while loosely supported on an arbor on the basis of said approximate average torque.

4. The method as in claim 3 in which said predetermined rotation is about 70 degrees.

* * * * *